United States Patent
Murthy et al.

[11] Patent Number: 5,919,931
[45] Date of Patent: Jul. 6, 1999

[54] PROCESS FOR THE MANUFACTURE OF INTERMEDIATES SUITABLE TO MAKE DOXAZOSIN, TERAZOSIN, PRAZOSIN, TIODAZOSIN AND RELATED ANTIHYPERTENSIVE MEDICINES

[75] Inventors: K. S. Keshava Murthy; Gamini Weeratunga; Tianhao Zhou; Bhaskar Reddy Guntoori, all of Brantford, Canada

[73] Assignee: Brantford Chemicals Inc., Brantford, Canada

[21] Appl. No.: 08/627,454

[22] Filed: Apr. 4, 1996

[51] Int. Cl.⁶ .................. C07D 405/06; C07D 413/06
[52] U.S. Cl. .................. 544/367; 544/374; 544/377; 544/379; 544/284; 544/291
[58] Field of Search .................. 544/367, 374, 544/377, 379, 284, 291

[56] References Cited

U.S. PATENT DOCUMENTS

| | | | |
|---|---|---|---|
| 4,001,238 | 1/1977 | Partyka et al. | 544/284 |
| 4,026,894 | 5/1977 | Winn et al. | 544/291 |
| 4,046,762 | 9/1977 | Manghisi et al. | 544/377 |
| 4,188,390 | 2/1980 | Campbell | 544/291 |
| 4,287,341 | 9/1981 | Hess et al. | 544/285 |
| 5,675,006 | 10/1997 | Karimian et al. | 544/293 |

FOREIGN PATENT DOCUMENTS

| | | |
|---|---|---|
| 2077252 | 3/1994 | Canada . |
| 2171997 | 9/1986 | United Kingdom . |

*Primary Examiner*—Emily Bernhardt
*Attorney, Agent, or Firm*—Ivor M. Hughes; Neil H. Hughes; Marcelo K. Sarkis

[57] ABSTRACT

A process is provided for the manufacture of:

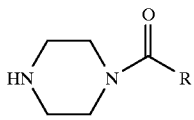

where R is:

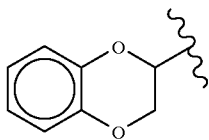

(Intermediate for Doxazosin)

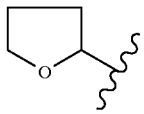

(Intermediate for Terazosin)

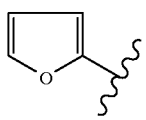

(Intermediate for Prazosin)

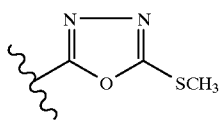

(Intermediate for Tiodazosin)

comprising reacting:

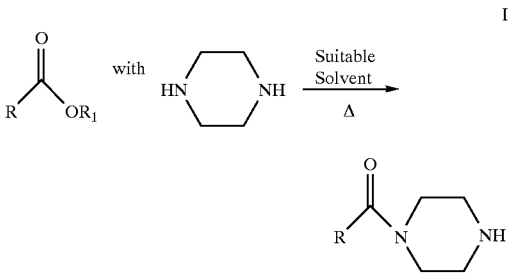

wherein $R_1$ may be selected from H, Methyl, Ethyl and suitable lower alkyl groups, $C_n H_{2n+1}$ (where n is from 3 to 5) or any other suitable group and thereafter if desired converting the resultant product to a salt thereof.

14 Claims, No Drawings

PROCESS FOR THE MANUFACTURE OF INTERMEDIATES SUITABLE TO MAKE DOXAZOSIN, TERAZOSIN, PRAZOSIN, TIODAZOSIN AND RELATED ANTIHYPERTENSIVE MEDICINES

FIELD OF INVENTION

This invention relates to a new process of making mono-N-Acyl piperazines from piperazine which are useful intermediates for the manufacture of Doxazosin, Terazosin, Prazosin, Tiodazosin and related antihypertensive medicines.

BACKGROUND OF THE INVENTION

A number of antihypertensive medicines are the chemical entities containing N,N'-substituted piperazines having one nitrogen acylated and the other linked to cyclized Guanidines of the general Formula 1.

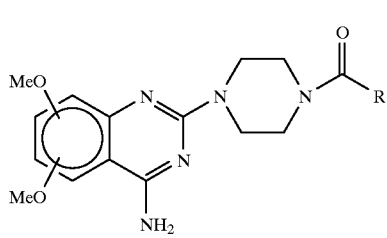

Formula 1

Suitable substituents for R may be those listed below:

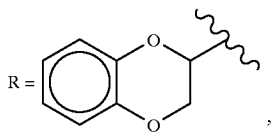

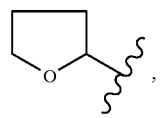

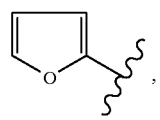

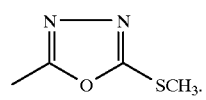

A number of antihypertensive medicines are the chemical entities of Formula 1 wherein the methoxy substituents are at the 6 and 7 positions as shown below in Formula 1A:

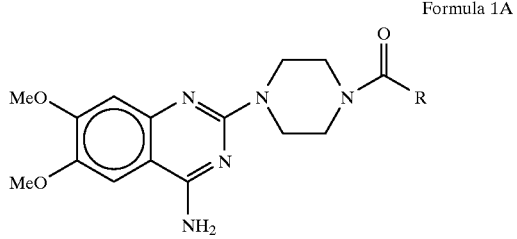

Formula 1A where

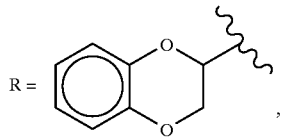

the medicine in Formula 1A is Doxazosin.

where

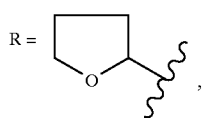

the medicine in Formula 1A is Terazosin.

where

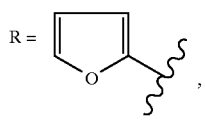

the medicine in Formula 1A is Prazosin.

where

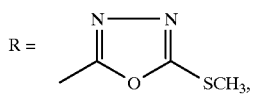

the medicine in Formula 1A is Tiodazosin.

The following compounds are thus presented:

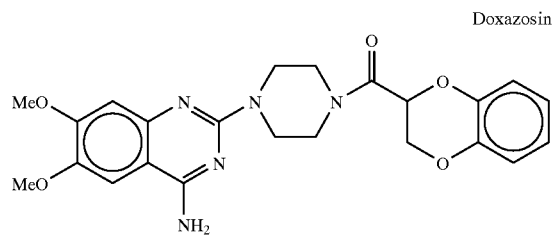

Doxazosin

Terazosin

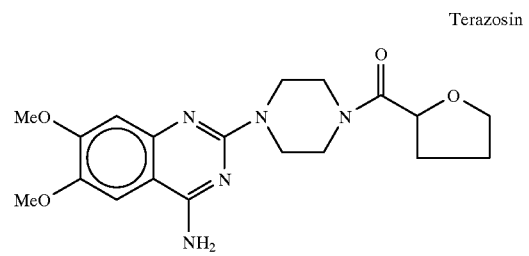

Prazosin

Tiodazosin

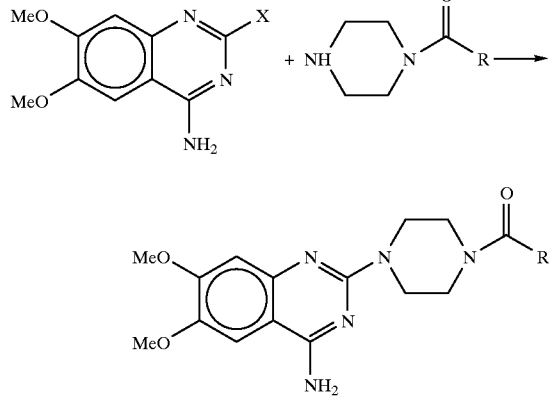

The compounds of general Formula 1 have been prepared by a number of approaches. One of the important approaches is that (Scheme 1) a 4-amino-6,7-dialkoxy quinazoline, substituted at C-9 position with a good leaving group X, is condensed with N-Acylated piperazines (see for example U.S. Pat. Nos. 4,093,726, 4,112,097 and 4,188,390, EP 0 028 473 Oct. 16, 1980; J. Med Chem. 1987, 30, 49–57 and references therein).

Scheme 1

Another approach (Scheme 2) involves the condensation of a urea derivative with N-Acylated piperazines and cyclization of the resultant urea derivatives with appropriate reagents to give the required products.

Scheme 2

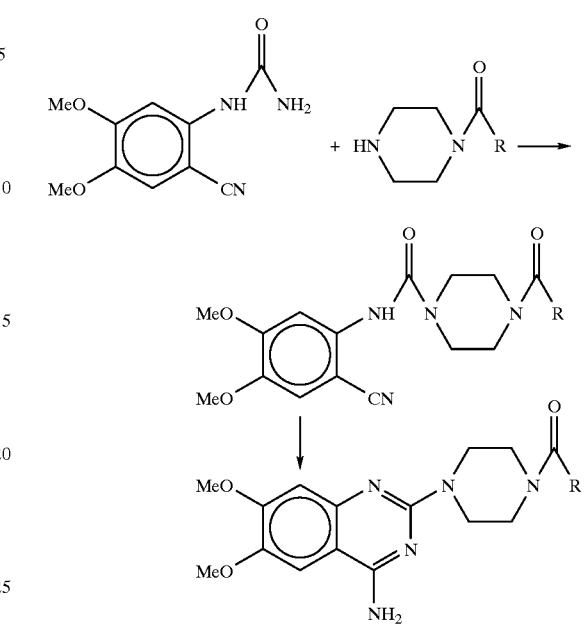

See Canadian Patent Application No. 2,077,252.

Both of the above methods use an N-Acyl piperazine as one of the active components. The N-Acyl piperazines of general Formula 2 have been prepared by a number of methods which may be classified into one general method. They all involve coupling reactions between an activated acid derivative A and piperazine (Scheme 3).

Formula 2

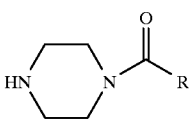

R may be selected from

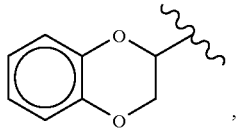

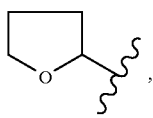

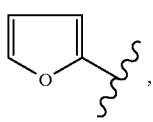 etc.

Scheme 3

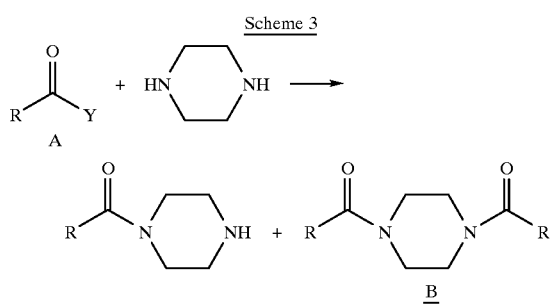

Y is

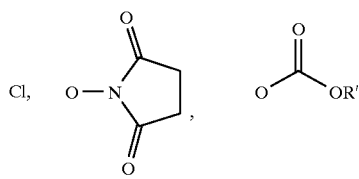

or other activating groups.

These activated acid derivatives (A) are generally prepared from corresponding acids or normal esters such as methyl, ethyl or other lower alkyl esters. Most of the processes taught by patents use acid chlorides (Y=Cl, Scheme 3) as activated acid derivatives (U.S. Pat. No. 4,188,390, Feb. 12, 1980; Canadian Patent No. 1,088,059, Oct. 21, 1980; U.S. Pat. No. 4,287,341, Sep. 1, 1981; EP Patent 0,028,473 Al, Oct. 16, 1980; U.K. Patent GB 2,171, 997A, Sep. 10, 1986). These patents explain the preparation of piperazine derivatives starts from normal esters. These esters are hydrolyzed using alkali to give acids, which are converted to acid chloride using $SOCl_2$ (thionyl chloride) or chemical equivalents of it. These acid chlorides react with piperazine in the presence of mineral acids, which involves tedious working up procedures, pH adjustment, and extractions in order to obtain acceptable yields (U.S. Pat. No. 4,287,371, Sep. 1, 1981; Canadian Patent No. 1,088,059, Oct. 21, 1980; U.S. Pat. No. 4,188,390, Feb. 12, 1980; EP patent No. 0,028,473 Al, Oct. 16, 1980; J. Med. Chem. 1977, 20, 146–149; J. Med. Chem. 1987, 30, 49–57). These reactions involve corrosive reagents such as Thionyl chloride or oxalyl chloride and one or more equivalents of concentrated mineral acids (Hydrochloric acid, Hydrobromic acid, etc.) The mineral acids are used to protect one of the two nitrogens of piperazine to avoid diacylated product (B, in Scheme 3). In Canadian Letters Patent No. 1,057,754, in order to prepare the N-(Tetrahydro-2-furoyl) piperazine, the patentee hydrogenates the N-(2-furoyl) piperazine (used to produce prazosin whose process of manufacture is taught in the prior art).

Other methods, not quite commonly used, employ succinimido and pthalimido esters as activating groups (U.S. Pat. No. 4,188,390, Feb. 12, 1980). These procedures are also not industrially viable as they involve expensive reagents and a number of steps

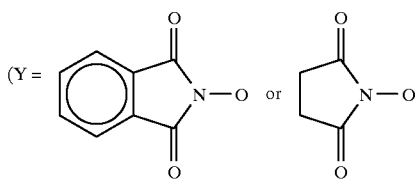

Scheme 3). For example, Succinimido ester is prepared conventionally by reacting the free acid with N-Hydroxy succinimide in presence of a dehydrating agent dicyclohexylcarbodiimide, which is highly toxic, corrosive and expensive (Review; Synthesis, 1981, 333 and references cited therein). This is the same with mixed anhydrides

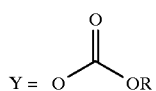

where R may be pivaloyl or isobutyl, Scheme 3).

It is therefore an object of this invention to provide a simple, new and efficient process for the synthesis of mono-N-Acyl piperazine derivatives which are useful and important intermediates used to manufacture quinazolines of general Formula 1 (eg. Doxazosin, Terazosin, Prazosin, Tiodazosin, etc.).

It is a further object of the invention to provide an improved, efficient and higher yielding process than those taught in the prior art.

It is still a further object of this invention to provide novel methods of preparing mono-N-Acyl piperazines including intermediates for Doxazosin, Terazosin, Prazosin and other antihypertensive medicines having an N-Acyl piperazine unit embodied in them.

Further and other objects of the invention will be realized by those skilled in the art from the following summary of invention and detailed description of embodiments thereof.

SUMMARY OF THE INVENTION

According to one aspect of the invention, a process of manufacture of

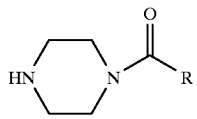

is provided where R is:

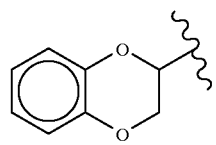 (Intermediate for Doxazosin)

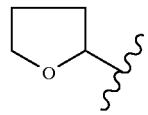 (Intermediate for Terazosin)

-continued

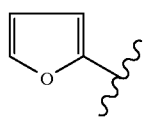
(Intermediate for Prazosin)

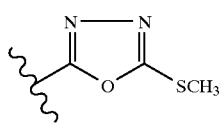
(Intermediate for Tiodazosin)

as follows:

Scheme 4

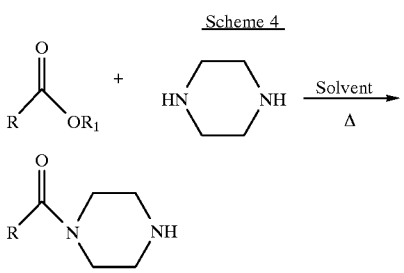

$R_1$ may be selected from (H, Methyl, Ethyl and other suitable lower alkyl groups, for example, $C_n H_{2n+1}$ (where n is from 3 to 5)).

The starting materials are known and may be made by methods known to persons skilled in the art or may be purchased where available. This invention provides a new, simple and efficient one-step procedure for producing mono-N-acylated piperazine derivatives using unactivated lower alkyl (for example, methyl, ethyl, and the like) esters and/or acids.

The use of these compounds employed in Applicants' invention does not involve:

1. The use of corrosive reagents such as thionyl chloride and oxalyl chloride to prepare the activated acids in the form of acid chlorides which involve in their preparation at least one extra step and sometimes two extra steps and use of concentrated mineral acids in the coupling reaction between the acid chloride and the piperazine (U.S. Pat. No. 4,188,390, Feb. 12, 1980; Canadian Patent No. 1,088,059, Oct. 21, 1990; J. Med. Chem, 1987, 30, 49–57; J. Med Chem., 1977, 20, 146–149; U.S. Pat. No. 4,287,341, Sep. 1, 1981; EP Patent No. 0,028,473 Al, Oct. 16, 1980) and 2. The use of imido esters and mixed anhydrides (U.S. Pat. No. 4,188,390, February 1980; Review: Synthesis, 1981, 333 and references cited therein) as activating groups, which are difficult to make and industrially not viable as they involve the use of expensive and highly toxic dehydrating reagents such as dicyclohexylcarbodiimide.

The present invention provides direct mono amidation of unactivated esters and acids with piperazine (Scheme 4) without using any activating reagents. Although direct amidation using amines and unactivated esters and acids is documented in the literature, amidation of piperazines poses problems as they have two nitrogens of equal reactivity, which can lead to diacylation product. This is often the case. For example, in Collection Czechoslovak Chem. Commun. 1985, 50, 1201–1211, authors reported amidation reactions of piperazine with methyl propionate and ethyl-2-hydroxy propionate. In the reaction with methyl propionate, one of the starting materials (methyl propionate) has been used in 12.5 equivalents excess and the reaction was carried out under reflux (boiling point of methyl propionate 79° C.) in the absence of any other solvent in order to achieve 30% maximum total yields. In another reaction with ethyl-2-hydroxy propionate, they heated reactants together without using any solvent for 150 hours to get 32% yield of required amide.

In another reported case (Eur. J. Med. Chem. 1989, 24, 233–240), the scientists reported amidation reaction using 6.67 eq of piperazine and a methyl ester compound. The reaction was done at reflux temperatures in MeOH for 16 hours and the yields were only 26%.

The above two examples show how difficult and unattractive this direct amidation procedure is. However, by proper manipulation of the reaction conditions and by choosing the right solvent system, Applicants provided unexpectedly, a reaction that provides the desired mono-acylated-piperazines, which reaction is very efficient and high yielding. The operating procedures of this reaction are very simple and do not use any activating groups and external reagents except for corresponding starting materials and an inert aromatic hydrocarbon solvent system. The procedure is scalable for industrial purposes and also make it environmentally friendly as it does not use hazardous and corrosive materials or reagents.

Applicants have found that the suitable solvents are xylene and toluene and that the appropriate reaction conditions preferably involve the use in the reaction of between about 1.5 to about 2.5 equivalents, preferably about 2 equivalents, of piperazine, with one equivalent of appropriate acid or ester (one equivalent of each provides less than optimal yields and results in diacyl products at reflux temperature of the solvent used).

Xylenes (which are preferred) have a reflux temperature of about 142° C., present as mixed isomers or one isomer. Toluene has a reflux temperature of about 110° C. If xylenes and toluene are mixed, the reflux temperature of the mixture is between the two.

Thus according to another aspect of the invention a process is provided comprising reacting:

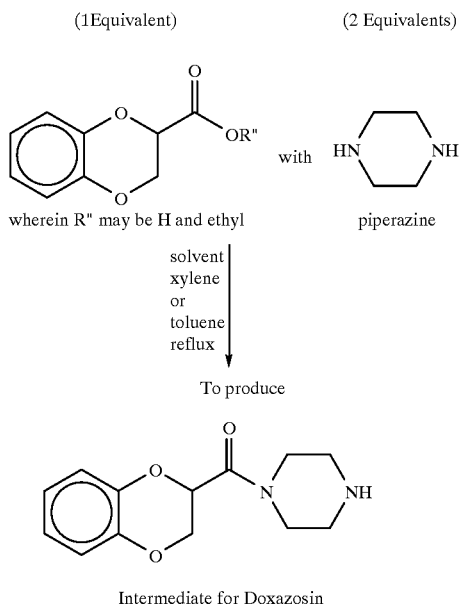

Intermediate for Doxazosin

According to another aspect of the invention, the following process is also provided:

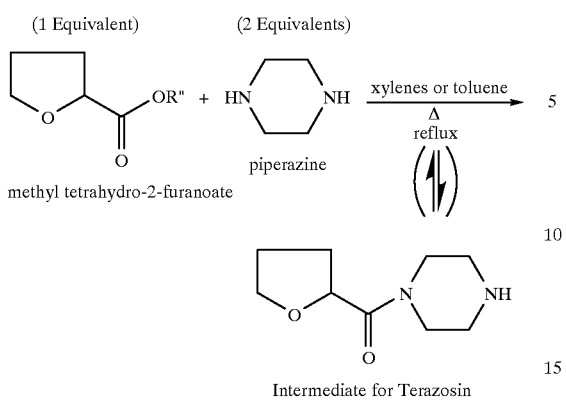

methyl tetrahydro-2-furanoate

Intermediate for Terazosin

R" is selected from H and Methyl

According to another aspect of the invention, the following process is also provided:

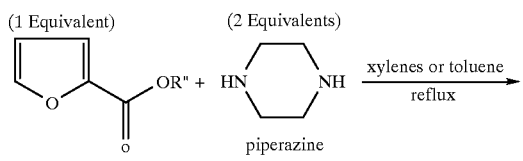

R" is selected from H and Methyl

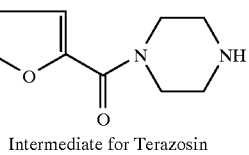

Intermediate for Terazosin

These reactions can be carried out in xylene (mixture of isomers) or toluene as solvent using piperazine at reflux temperatures. The optimal amount of piperazine used is 2 equivalents with respect to starting material. These amounts may however be varied over a broad range. The products can be worked up directly or as the salt form using 1.1 equivalent of concentrated hydrochloric acid. The pure salts can be precipitated in isopropanol at room temperature or at 0° C. Other solvent mixtures also can be used for precipitation.

This invention will now be illustrated with respect to the following detailed description of embodiments of the invention.

Example 1

Preparation of N-(1,4-Benzodioxane-2-Carbonyl) Piperazine Hydrochloride

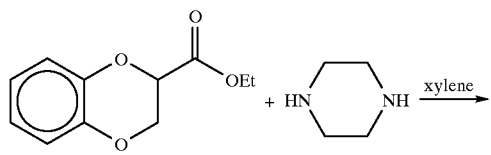

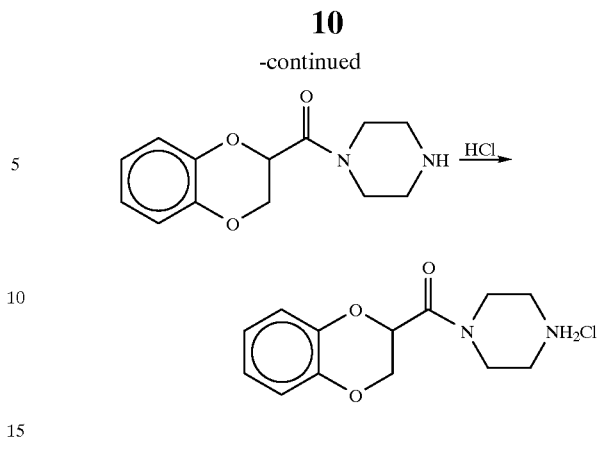

A suspension of piperazine (165.5 g, 1.92 mol) in xylenes (1000 mL) was added to the ethyl ester (200 g, 0.961 mol). The mixture was heated to reflux for 26.5 hours. Then the reaction mixture was washed by brine (500 mL). The organic layer and the aqueous layer were separated and the aqueous layer was extracted with ethyl acetate (3×500 mL). The organic layers were combined and concentrated. Then isopropanol (1000 mL) was added, followed by concentrated HCl (960 mL, 1.15 mol). The slurry like mixture was stirred at 0° C. for 20 minutes. The precipitate was filtered and dried under vacuum for 24 hours to give 209.4 g of product (77% yield).

Example 2

Preparation of N-(1,4-Benzodioxane-2-Carbonyl) Piperazine Hydrochloride

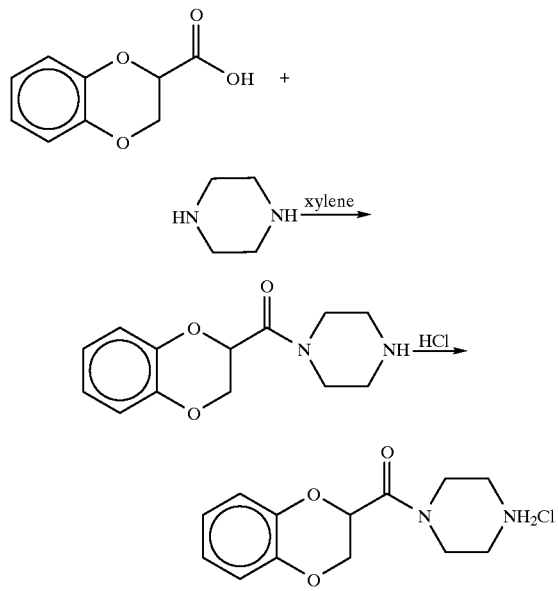

To a suspension of piperazine (23.90 g, 0.278 mol) in xylenes (125 mL) was added the acid (25 g, 0.139 mol) portionwise, under reflux conditions. The reaction mixture was refluxed for 75 hours and brine (150 mL) was added. The organic layer was separated and the aqueous layer was extracted with ethyl acetate (3×100 mL). The organic layers were combined and concentrated. Then isopropanol (125 mL) was added followed by concentrated HCl (9.70 mL, 0.0967 mol). The slurry like mixture was stirred at 0° C. to −5° C. for 30 minutes. The precipitate was filtered and dried under vacuum to give 20.0 g product (50% yield).

Example 3

Preparation of N-(Tetrahydrofuran-2-Carbonyl) Piperazine

To a suspension of piperazine (66.2 g, 0.768 mol) in xylenes (500 mL) was added methyl tetrahydro 2-furanoate (50.0 g, 0.384 mol) and the resulting reaction mixture was refluxed for 28 hours. The reaction was cooled to 0° C. for 1.5 hours and filtered. The filtrate was concentrated in vacuo to yield 56.1 g of the expected product (79% yield).

Example 4

Preparation of N-(Tetrahydrofuran-2-Carbonyl) Piperazine

A suspension of piperazine (7.23 g, 0.084 mol) in xylenes (50 mL) was added tetrahydro 2-furanoic acid (4.85 g, 0.042 mol). The mixture was heated to reflux for 28 hours. The reaction mixture was cooled to room temperature and filtered. The filtrate was concentrated to give 3.53 g of product (46% yield).

Example 5

Preparation of N-2-Furoyl Piperazine

To a suspension of piperazine (69.68 g, 0.8091 mol) in xylenes (100 mL) was added (50.00 g, 0.3965 mol) of methyl 2-furoate. The formed reaction mixture was refluxed for 18 hours. The unreacted piperazine was filtered and the filtrate was concentrated under vacuum to give 47.0 g (0.2608 mol) of required product (64% yield).

As many changes can be made to the embodiments without departing from the scope of the invention, it is intended that all material herein be interpreted as illustrative of the invention.

The embodiments of the invention in which an exclusive property or privilege is claimed are as follows:

1. A process for the manufacture of:

where R is:

[(Intermediate for Doxazosin)]

[(Intermediate for Terazosin)]

[(Intermediate for Prazosin)]

[(Intermediate for Tiodazosin)]

consisting essentially of reacting:

I

[a solvent selected from the group consisting of xylenes and toluene]

wherein said reaction occurs in the presence of a solvent selected from the group consisting of xylenes and toluene, and wherein $R_1$ is selected from the group consisting of H, Methyl, Ethyl, propyl, butyl and pentyl and thereafter if desired converting the resultant product to a salt thereof, wherein between about 1.5 to about 2.5 equivalents of piperazine are reacted with each equivalent of Compound I.

2. The process of claim 1 wherein about 2 equivalents of piperazine are reacted with each equivalent of Compound I.

3. The process of claim 1 or 2 wherein the solvent is xylene.

4. The process of claim 1 or 2 wherein the solvent is toluene.

5. The process of claim 1 of reacting:

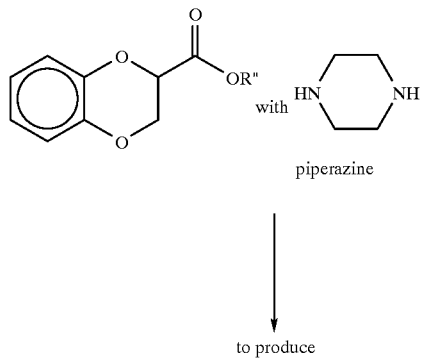

and thereafter reflux,
wherein R" may be selected from H and ethyl.

6. The process of claim 1 of reacting:

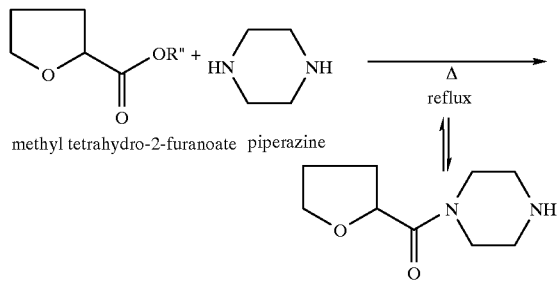

wherein R" may be selected from H and Methyl.

7. The process of claim 1 of reacting:

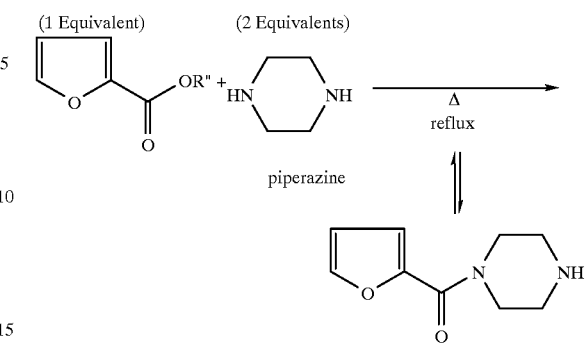

wherein R" may be selected from H and Methyl.

8. The process according to claim 1 of preparing N-(1,4-Benzodioxane-2-Carbonyl) Piperazine Hydrochloride by reacting:

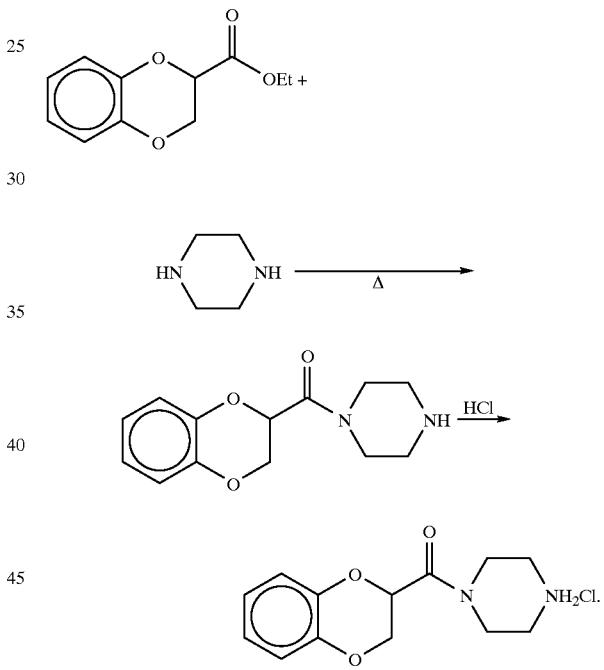

9. The process according to claim 1 of producing N-(1,4-Benzodioxane-2-Carbonyl) Piperazine Hydrochloride by reacting:

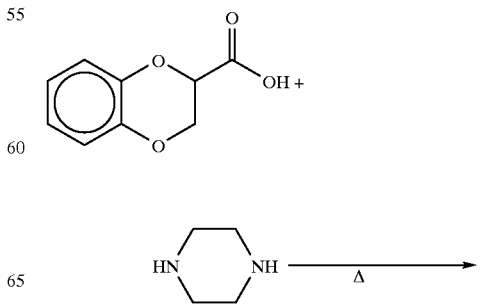

-continued

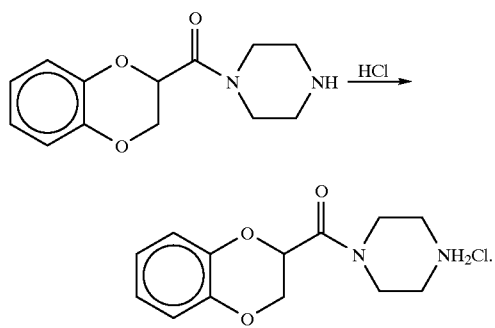

10. The process according to claim 1 of producing N-(Tetrahydrofuran-2-Carbonyl) Piperazine by reacting:

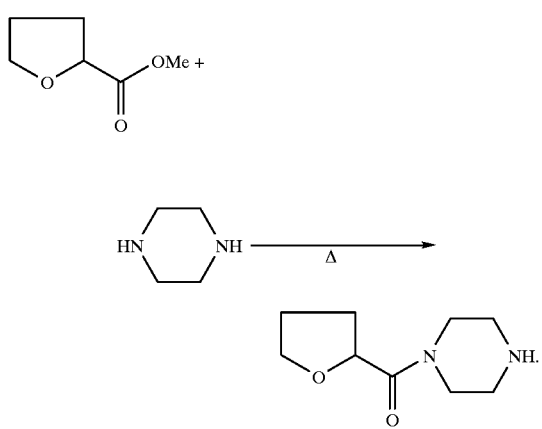

11. The process according to claim 1 of producing N-(Tetrahydrofuran-2-Carbonyl) Piperazine by reacting:

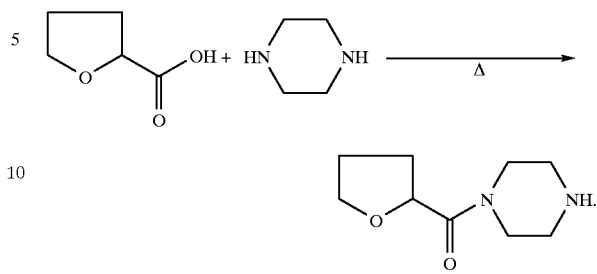

12. The process according to claim 1 of producing N-2-Furoyl Piperazine by reacting:

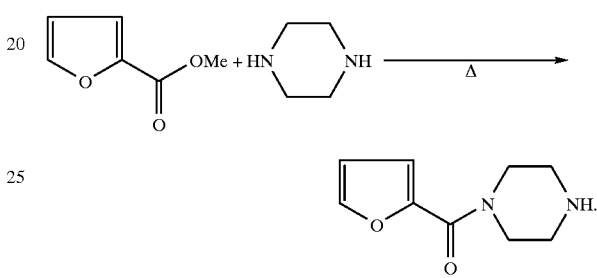

13. The process of claim 1, 3 or 4 wherein the solvent is xylene.

14. The process of claim 1, 3 or 4 wherein the solvent is toluene.

* * * * *